(12) United States Patent
Joerger

(10) Patent No.: US 10,849,573 B2
(45) Date of Patent: Dec. 1, 2020

(54) METHOD AND APPARATUS FOR ENSURING CORRECT POSITIONING FOR A RADIOGRAPHY RECORDING

(71) Applicant: Siemens Healthcare GmbH, Erlangen (DE)

(72) Inventor: Clemens Joerger, Forchheim (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/223,287

(22) Filed: Dec. 18, 2018

(65) Prior Publication Data
US 2019/0183438 A1    Jun. 20, 2019

(30) Foreign Application Priority Data
Dec. 20, 2017 (DE) .................. 10 2017 223 440

(51) Int. Cl.
*A61B 6/08* (2006.01)
*A61B 6/04* (2006.01)
*A61B 6/00* (2006.01)

(52) U.S. Cl.
CPC .................. *A61B 6/04* (2013.01); *A61B 6/46* (2013.01); *A61B 6/461* (2013.01); *A61B 6/463* (2013.01);
(Continued)

(58) Field of Classification Search
CPC ........... A61B 6/04; A61B 6/465; A61B 6/487; A61B 6/485; A61B 6/46; A61B 6/463;
(Continued)

(56) References Cited

U.S. PATENT DOCUMENTS

| 8,730,314 B2 | 5/2014 | Hannibal et al. |
| 10,154,239 B2 | 12/2018 | Casas |

(Continued)

FOREIGN PATENT DOCUMENTS

| DE | 10250571 A1 | 7/2003 |
| DE | 102012201798 A1 | 8/2013 |

(Continued)

OTHER PUBLICATIONS

German Office Action dated Dec. 20, 2018.
(Continued)

*Primary Examiner* — Kiho Kim
(74) *Attorney, Agent, or Firm* — Harness, Dickey & Pierce, P.L.C.

(57) ABSTRACT

A method and apparatus are disclosed for ensuring correct positioning for a radiography recording. The method includes providing an examination request of the body region; pre-positioning the body region in the radiography system for the radiography recording; pre-positioning at least one of a recording unit of the radiography system and an image detector of the radiography system for the radiography recording; producing a positioning recording of the body region via the radiography system, the radiography system being switched into the fluoroscopy mode and the positioning recording being a fluoroscopy recording; producing positioning information from the positioning recording; and outputting the positioning information.

25 Claims, 3 Drawing Sheets

(52) U.S. Cl.
CPC .............. *A61B 6/465* (2013.01); *A61B 6/469* (2013.01); *A61B 6/485* (2013.01); *A61B 6/487* (2013.01); *A61B 6/5235* (2013.01); *A61B 6/54* (2013.01); *A61B 6/587* (2013.01)

(58) Field of Classification Search
CPC ......... A61B 6/587; A61B 6/5235; A61B 6/54; A61B 6/461
See application file for complete search history.

(56) References Cited

U.S. PATENT DOCUMENTS

| | | |
|---|---|---|
| 2003/0081734 A1 | 5/2003 | Nicolas et al. |
| 2009/0168966 A1 | 7/2009 | Suzuki et al. |
| 2012/0155609 A1 | 6/2012 | Lemminger et al. |
| 2016/0073975 A1 | 3/2016 | Hefetz et al. |
| 2016/0073979 A1 | 3/2016 | Braun et al. |
| 2016/0089094 A1 | 3/2016 | Kawamura et al. |
| 2016/0213329 A1 | 7/2016 | Dirkes |
| 2017/0100089 A1 | 4/2017 | Chang et al. |
| 2017/0112456 A1* | 4/2017 | Ohga ..................... A61B 6/469 |
| 2017/0119338 A1 | 5/2017 | Merckx |
| 2017/0312032 A1* | 11/2017 | Amanatullah ......... A61B 34/10 |
| 2017/0322484 A1* | 11/2017 | Erhard ................... A61B 6/467 |
| 2018/0021000 A1* | 1/2018 | Akiyama ............... A61B 6/481 378/62 |
| 2018/0140270 A1 | 5/2018 | Profio et al. |
| 2018/0160995 A1* | 6/2018 | Akiyama ................ G06T 19/00 |
| 2018/0182102 A1 | 6/2018 | Jerebko et al. |
| 2019/0000407 A1 | 1/2019 | Muller et al. |

FOREIGN PATENT DOCUMENTS

| | | |
|---|---|---|
| DE | 102015201070 A1 | 7/2016 |
| EP | 3387997 A1 | 10/2018 |

OTHER PUBLICATIONS

European Office Action dated Nov. 12, 2019.
European Search Report for Patent Application No. EP17209022.7 dated Jul. 12, 2018.
United States Notice of Allowance for U.S. Appl. No. 16/223,286, dated May 20, 2020.

* cited by examiner

METHOD AND APPARATUS FOR ENSURING CORRECT POSITIONING FOR A RADIOGRAPHY RECORDING

PRIORITY STATEMENT

The present application hereby claims priority under 35 U.S.C. § 119 to German patent application number DE 102017223440.7 filed Dec. 20, 2017, the entire contents of which are hereby incorporated herein by reference.

FIELD

Embodiments of the invention generally relate to a method and an apparatus for positioning a body region for a radiography recording via a radiography system, in particular a positioning aid which is controlled via fluoroscopy in the field of radiography. At least one embodiment of the invention further relates to a control apparatus for a radiography system and to a corresponding radiography system.

BACKGROUND

In addition to methods such as computer tomography or magnetic resonance tomography, radiography is an important part of radiology. In addition to the standard radiography systems, combined radiography-fluoroscopy devices (e.g. Luminos dRF) have become established in recent years.

In radiography, the object to be recorded (e.g. a knee, a wrist or an ankle) is positioned by specialist staff in such a way that a useful recording is produced for the current examination. It is however often the case that the alignment and/or positioning of the object or elements to be recorded was not optimal, and therefore the object in the recording is e.g. displaced, part of the object is truncated, or the object is depicted from an incorrect recording angle.

The quality of the positioning is usually assessed with reference to the recorded X-ray image, generally using the experience of the specialist staff or based on subjective perception. If the positioning was not correct, a further recording must be produced, signifying an additional dose for the patient and more time spent by the specialist staff. This represents a disadvantage for the patient and the specialist staff. In addition, every additional recording reduces the service life of the radiography system.

A technical solution is not currently available. In the case of images which cannot be diagnosed, a new recording must be performed.

SUMMARY

An embodiment of the present invention specifies an alternative convenient method and a corresponding apparatus and control entity for controlling a radiography system, by which it is possible to avoid at least one of the disadvantages described above.

Embodiments of the present invention are directed to a method, an apparatus, a control entity and a radiography system.

An inventive control entity of at least one embodiment, for controlling a radiography system, is designed to perform a method according to at least one embodiment of the invention and/or comprises an apparatus according to at least one embodiment of the invention.

An embodiment of the present invention is directed to a method for positioning a body region of a patient for a radiography recording via a radiography system designed for recordings in a context of both radiography and fluoroscopy, the method comprising:
a) providing an examination request of the body region;
b) pre-positioning the body region in the radiography system for the radiography recording;
c) pre-positioning at least one of a recording unit of the radiography system and an image detector of the radiography system for the radiography recording;
d) producing a positioning recording of the body region via the radiography system, the radiography system being switched into the fluoroscopy mode and the positioning recording being a fluoroscopy recording;
e) producing positioning information from the positioning recording; and
f) outputting the positioning information.

An embodiment of the present invention is directed to an apparatus for positioning a body region of a patient for a recording via a radiography system designed for recordings in the context of both radiography and fluoroscopy, the apparatus comprising:
a data interface to receive an examination request in respect of the body region;
an interface to control a motional unit for pre-positioning a recording unit of the radiography system;
an interface to control production of a positioning recording of the body region via the radiography system;
an interface to receive fluoroscopy recordings from the radiography system;
a production unit to produce positioning information from the positioning recording; and
an output unit to output the positioning information.

An inventive radiography system comprises a control entity according to at least one embodiment of the invention.

A significant proportion of the components cited above in respect of the apparatus or the control entity can be realized in the form of software modules in a processor of a corresponding apparatus or control entity respectively. A largely software-based realization has the advantage that computing systems or control entities already in use can also be upgraded easily by way of a software update in order to function in the inventive manner.

To this extent, at least one embodiment of the invention is directed to a corresponding computer program product comprising a computer program which can be loaded directly into a computing system or a storage entity of a control entity of a radiography system and has program sections for executing at least one embodiment of the inventive method when the program is executed in the computing system or the control entity. In addition to the computer program, such a computer program product may comprise additional elements such as e.g. documentation and/or additional components including hardware components such as e.g. hardware keys (dongles, etc.) for using the software.

For transportation to the computing system or the control entity and/or for the purpose of storage at or in the computing system or the control entity, it is possible to use a computer-readable medium, e.g. a memory stick, a hard disc or other transportable or integrated data medium, on which are stored the program sections of the computer program that can be read in and executed by a computing system or a computer unit of the control entity. For this purpose, the computer unit may have e.g. one or more interworking microprocessors or similar.

BRIEF DESCRIPTION OF THE DRAWINGS

The invention is explained again in greater detail below with reference to example embodiments and to the appended figures. Identical components in the various figures are denoted by identical reference signs in this case. The figures are generally not to scale.

DETAILED DESCRIPTION OF THE EXAMPLE EMBODIMENTS

Figure 1:
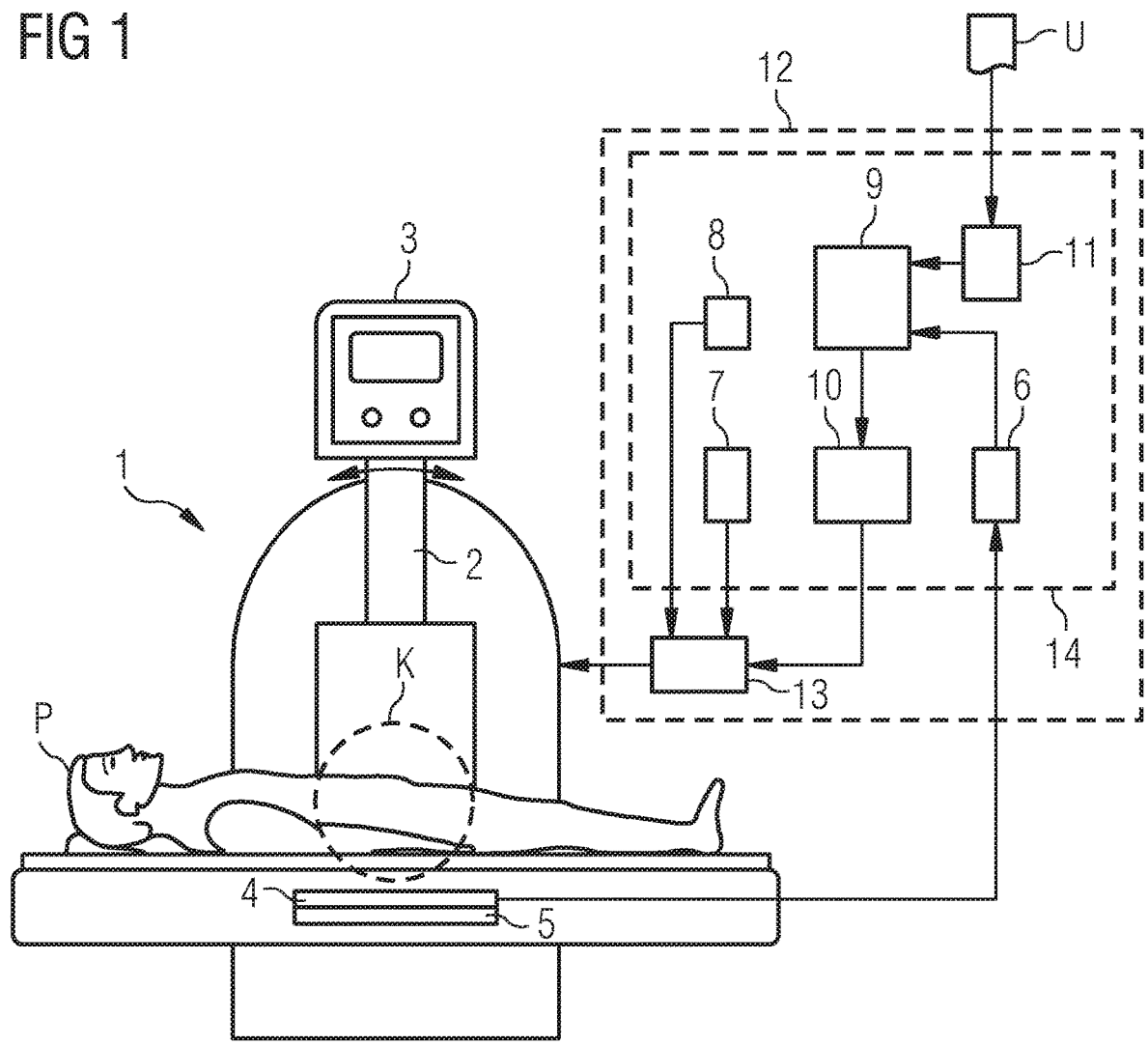
FIG. 1 shows a simple schematic diagram of a preferred radiography system with an example embodiment of an apparatus according to the invention for performing the method.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

In order to allow a better understanding of the following explanations, it is first clarified that a radiography system in the sense of the invention is understood to be a system for projection radiography and not for sectional image methods (tomography). More precisely, this term is understood to comprise a system which is designed for combined radiography-fluoroscopy. Therefore regions of the body of the patient are penetrated by X-radiation from a direction. On the other side, the radiation is registered by suitable materials (e.g. film or a spatially resolving detector) and a projection image which is usually two-dimensional is produced thereby. Systems for computer tomography or corresponding systems are not radiography systems in the sense of the invention. The advantages of the invention are shown to be particularly impressive in the field of two-dimensional radiography recordings.

An embodiment of the present invention is directed to a method for positioning a body region of a patient, which may be a human but may also be an animal, for a radiography recording, this being two-dimensional in particular, via a radiography system which is designed for recordings in the context of both radiography and fluoroscopy, the method comprising:

a) Providing an Examination Request

In this step, the method is told which body region is concerned, e.g. which bone or which organ, and which recording is to be performed. The examination request may simply comprise a reference to the body region, e.g. "knee AP" or "knee lateral". An organ program which is included in an examination request can also be provided in addition to the examination request.

b) Pre-Positioning the Body Region

The body region for the radiography recording is pre-positioned in the radiography system. For this purpose, e.g. the patient is positioned in such a way that the relevant body region is aligned above a spatially resolving image detector.

c) Pre-Positioning the Recording Unit/Image Detector

For this purpose, the recording unit and/or the image detector of the radiography system are positioned in an appropriate manner for the radiography recording. This positioning should take place in accordance with the examination request. If the examination request includes corresponding control instructions or the method has access to a database containing control instructions which are associated with information from an examination request, this pre-positioning can take place automatically.

d) Producing a Positioning Recording

A positioning recording of the body region of the patient is made by the radiography system, wherein the positioning recording is a fluoroscopy recording. For this purpose, the radiography system is switched into the fluoroscopy mode if it is not already in this mode, in order that it can make one or more fluoroscopic recordings.

Using fluoroscopy, an X-ray image can be produced using a much smaller dose than is required for the actual radiography recording. The fluoroscopy can also be used to observe movements. Therefore fluoroscopy allows positioning relative to an object using a very small radiation dose.

The positioning recording is produced while the body region is in the position adopted in step b). If the patient has moved, this can also be considered as pre-positioning in the context of the invention, since step b) can also readily take place after step c).

e) Producing Positioning Information

The positioning information is produced from the positioning recording.

For the purpose of producing the positioning information, an image processing system can be used which, for example, performs a correlation of the positioning recording with reference recordings or by processing the positioning recording in an algorithm which is correspondingly trained on the basis of machine learning. The processing of the positioning recording preferably includes a correlation of this positioning recording with the examination request, i.e. a check to determine whether this is actually the desired body region, for example. According to a preferred alternative or development, a correlation of this positioning recording with good reference radiography images takes place as part of the processing the positioning recording. According to a further preferred alternative or development, the processing can be analytical. In this case, the quality-critical criteria (e.g. the joint space of the knee) are visualized on the positioning recording, analyzed (e.g. by measuring the width of the joint space of the knee) and the result is displayed to the user. It is therefore possible to provide a live display, for example, in which the joint space of the knee is displayed with a size scale and/or the measured width and, in particular, a display in the form of e.g. a traffic light illustrating the quality of the positioning is also displayed.

f) Output

In this step, provision is made for outputting at least the positioning information, preferably together with further data such as e.g. a preview image.

The additional display of a preview image has the advantage that an operator then has an additional way of deciding whether the settings at the system or the pre-positionings are suitable or must be corrected. By virtue of the positioning information, the decision of the operator can be made much more quickly and efficiently than is possible without this information.

One example is a knee AP recording. For this recording, it is very important for the joint space of the knee to be visible on the X-ray image. This means that the X-ray beam must pass tangentially through this joint space. This is achieved by correct positioning of the patient and/or the recording unit. When the fluoroscopy is used, the device can then display how good the radiography image will be via an indicator (positioning information). For example, a red to green range could also be defined: if the display is in the green range, a radiography recording can be produced. In order to arrive in the green range, the patient or the recording unit must be repositioned if applicable.

In the case of an overview recording of the pelvis or thorax, the priority would be to achieve a suitable overlay. The device would therefore show the green indicator if everything of anatomical importance (e.g. apexes of the lungs) was contained in the recording. If the recording region was too big, the indicator would become red again.

At least one embodiment is directed to an apparatus for positioning a body region of a patient for a radiography recording via a radiography system, which is designed for recordings in the context of both radiography and fluoroscopy, the apparatus comprising:

A data interface for providing an examination request in respect of the body region. This interface can be a data interface to an input unit by which a user can input the examination request manually, e.g. a computer or simply a keypad.

An interface for pre-positioning a recording unit of the radiography system. For example, this interface can control a motional unit (or send relevant control data to a control unit) which can move the recording unit.

In a specifically preferred embodiment, the apparatus also comprises a pre-positioning display unit by which the desired positioning of the body region can be displayed.

Furthermore, the apparatus preferably has sensors which can measure the positioning of a body region in a radiography system. It is then possible to check whether a body region has been pre-positioned correspondingly.

A recording control interface for controlling the production of a positioning recording of the body region via the radiography system. By way of this recording control interface, the recording unit is directly or indirectly activated via a further control interface of a control entity. In addition to the instruction to start a recording, the recording control interface can also be used to send control instructions relating to special recording parameters, e.g. energy data or specifications of an exposure time or a collimator setting.

An image data interface for receiving fluoroscopy recordings from a radiography system. This is preferably a direct interface for receiving the data from the image detector of the radiography system or an interface for receiving pre-processed image data.

In summary, the recording control interface starts a recording and the image data interface receives it.

A production unit for producing positioning information from the positioning recording. For the purpose of producing the positioning information, which comprises displayable information or data for further automatic processing by a computer, an automatic examination of the positioning recording or of a preview image based on this positioning recording is preferably carried out in order to determine whether the body region is correctly represented for the radiography recording.

An output unit for outputting the positioning information.

An inventive control entity of at least one embodiment, for controlling a radiography system, is designed to perform a method according to at least one embodiment of the invention and/or comprises an apparatus according to at least one embodiment of the invention.

An inventive radiography system comprises a control entity according to at least one embodiment of the invention.

A significant proportion of the components cited above in respect of the apparatus or the control entity can be realized in the form of software modules in a processor of a corresponding apparatus or control entity respectively. A largely software-based realization has the advantage that computing systems or control entities already in use can also be upgraded easily by way of a software update in order to function in the inventive manner.

To this extent, at least one embodiment of the invention is directed to a corresponding computer program product comprising a computer program which can be loaded directly into a computing system or a storage entity of a control entity of a radiography system and has program sections for executing at least one embodiment of the inventive method when the program is executed in the computing system or the control entity. In addition to the computer program, such a computer program product may comprise additional elements such as e.g. documentation and/or additional components including hardware components such as e.g. hardware keys (dongles, etc.) for using the software.

For transportation to the computing system or the control entity and/or for the purpose of storage at or in the computing system or the control entity, it is possible to use a computer-readable medium, e.g. a memory stick, a hard disc or other transportable or integrated data medium, on which are stored the program sections of the computer program that can be read in and executed by a computing system or a computer unit of the control entity. For this purpose, the computer unit may have e.g. one or more interworking microprocessors or similar.

Further particularly advantageous embodiments and developments of the invention are derived from the dependent claims and from the following description, wherein the claims in one class of claim can be developed in a similar manner to the claims and description parts relating to another class of claim and in particular individual features of various example embodiments and variants can also be combined to form further example embodiments and variants.

A preview image is preferably initially produced from the positioning recording, wherein the preview image simulates the radiography recording as it would be recorded using the existing pre-positioning of the radiography system, i.e. using the corresponding pre-positioning of the image detector and the recording unit. If the same image detector and the same recording unit that were used for the fluoroscopy recording are correctly used for the radiography recording, this will automatically result in e.g. a recording from the same viewing angle. In the event that different image detectors are used, either the positioning recording must be adapted correspondingly via image processing or the detection unit that is used must be positioned correspondingly for the radiography recording.

The positioning information is then preferably produced from the preview image. For the purpose of manually checking the positioning information or further assessing the quality of a radiography recording, it is particularly advantageous to output the preview image together with the positioning information.

The presettings are preferably effected in the inventive method in accordance with the examination request, wherein the examination request preferably includes an organ program or an organ program is provided in addition to the examination request. Correlation of the positioning recording with this organ program preferentially takes place as part of this activity.

In addition to the positioning, the examination request preferably specifies additional recording parameters for the radiography system, e.g. recording energy, exposure time and collimator setting. In this case, the preview image preferably simulates a radiography recording which would be recorded using these recording parameters. This can be done via corresponding image processing, for example. If the same recording unit is used, the recording energy for e.g. the fluoroscopy recording can be set so as to be identical to the recording energy for the radiography recording, the exposure time being then selected such that the possibly lower dose of the fluoroscopy recording and the possibly higher sensitivity of the image detector are taken into consideration when calculating the preview image. A suitable conversion function can be produced from reference recordings.

For the purpose of producing the positioning information, provision is preferably made for correlating the positioning recording or the preview image with existing radiography images. In this context, provision is preferably made likewise for the positioning recording and/or the preview image to be automatically examined or correlated as a function of the requirements of the examination request, and/or for analytical processing as stated above. The positioning information in this context indicates whether the body region and the recording unit are correctly positioned for the radiography recording based on the examination request.

The correspondingly preferred apparatus comprises as required a database containing reference radiography images, wherein the production unit is designed to correlate the positioning recording and/or a preview image based on this positioning recording with the reference radiography images of the database. The production unit is preferably also designed to perform an automatic examination of the positioning recording and/or the preview image as a function of the requirements of the examination request and to produce positioning information which indicates whether the body region and the recording unit are correctly positioned for the radiography recording based on the examination request.

The positioning recording is preferably made via the recording unit and an image detector of the radiography system. Therefore only elements which are already present in the radiography system and no further elements are used for the purpose of recording the image data. Depending on the application case, the radiography system preferably comprises, in addition to an image detector for the fluoroscopy recording, a further detection unit for the radiography recording. This has the advantage that the detection unit for the radiography recording can be optimized, e.g. providing a higher image resolution. The image detector for the fluoroscopy recording can be optimized for a good representation even when using a low dose (e.g. owing to low image noise).

The positioning information is preferably output visually and/or acoustically, most preferably in the form of an indicator whose design in the event of incorrect positioning is different from its design in the event of correct positioning. Provision is preferably made in this case for the color and/or the brightness of the indicator to be changed as soon as a correct positioning is achieved.

The positioning information preferably contains details indicating whether or not the preview image is acceptable based on the examination request, and if not, additional information indicating which settings must be adapted, e.g. collimator settings or position/rotation of the display unit or the body region. If a pre-positioning has changed, the positioning information most preferably includes information showing whether or not this change resulted in an improvement of the positioning.

The radiography system is preferably controlled in such a way that at least the steps c)-f) of at least one embodiment the inventive method are performed using different pre-positionings of the recording unit. Even if a given embodiment does not require this, a different pre-positioning of the body region is also effected in accordance with step b) in particular.

The method steps cited above are executed until the positioning information displays a correct positioning of the recording unit based on the examination request, and a radiography recording is then made accordingly, preferably automatically, via the recording unit.

If a presetting is incorrect, a presetting is repeated or the existing presettings are changed, a positioning recording is made again, and a preview image is generated and output automatically. If the preview image is correct, the radiography recording can be performed.

It is assumed in the following explanations that the radiography system 1 is a conventional X-ray device. However, the method can in principle be employed in other digital radiography systems 1 having a fluoroscopy function.

FIG. 1 shows a simple schematic diagram of a radiography system 1 for combined radiography-fluoroscopy, having a control entity 12 which is designed to perform the method according to the invention. As is customary, the radiography system 1 has a recording unit 3, which represents an X-ray source in this case and which irradiates a patient P during a fluoroscopy recording or a radiography recording R, such that the radiation strikes a detector system 4, 5 that is situated opposite the recording unit 3 in each case. Two image detectors are shown in the case illustrated here. One detector unit 5 is used specifically for the radiographic recordings and one image detector 4 is used specifically for the fluoroscopic recordings. It is entirely possible to use a single image detector for all recordings instead of the two image detectors 4, 5 shown. The image detector 4 for the fluoroscopy recording here is a digital, spatially resolving image receiver. The detector unit 5 for the radiographic recordings can likewise be such a digital detector, but can theoretically also be a holder for a film material. The recording unit 3 can be moved via a motional mechanism 2, a swivel arm here, e.g. raised or lowered, swiveled or rotated. In practice, the motional mechanism 2 should allow a plurality of different movements, such that the recording unit can be moved in an optimal manner in respect of its height, lateral position and inclination angle.

With regard to the control entity 12, only those components are illustrated which are essential for the explanation of the invention. Conventional radiography systems and associated control entities are in principle known to a person skilled in the art and therefore need not be explained in detail.

The radiography system 1 can be controlled by the control entity 12 via a control interface 13, i.e. the motional mechanism 2 is controlled for the purpose of moving the recording unit 3 or a fluoroscopy or radiography recording is started, for example. The recording unit 3 can also receive a setting via the control interface 13, e.g. in respect of the exposure time or the beam energy.

Neither a user interface nor an acquisition interface for the recorded image data nor an image data reconstruction unit are marked in, though the control unit 12 can obviously also comprise such elements.

The control entity 12 comprises an apparatus 14 for positioning a body region K of a patient P for a radiography recording R. In the case shown, this apparatus 14 does not act directly on the radiography system 1, but via the control interface 13 of the control entity 12.

The apparatus 14 comprises an interface 11 for the provision of an examination request U in respect of the body region K. In the case shown, it receives an examination request U from the outside, which can be entered e.g. via a user interface. A user interface of the control entity 12 can readily be used for this purpose.

A pre-positioning of a recording unit 3 of the radiography system 1 can be achieved via a pre-positioning interface 7. Here the pre-positioning interface 7 sends the data for the positioning to the control interface 13 of the control entity 12, and the latter controls the motional mechanism 2 and thereby positions the recording unit 3 in accordance with the specifications of the pre-positioning interface 7.

The apparatus 14 comprises two further data interfaces which are relevant for the positioning recordings PA. The first of these data interfaces, namely the recording control interface 8, switches the radiography system 1 into fluoroscopy mode if applicable and starts a fluoroscopy recording. The second of these data interfaces, namely the image interface 6, receives this fluoroscopy recording as positioning recording PA.

This positioning recording PA is then provided to the production unit 9 and the examination request U is likewise provided to the production unit 9 via the interface 11. The positioning recording PA and possibly the examination request U are used to produce the positioning information PI, possibly by way of a preview image VB, wherein the positioning information PI in this case returns the same viewing angle for a possible subsequent radiography recording since the recording unit 3 is the same.

The positioning information PI and possibly a preview image VB can be output via an output unit 10. The output unit 10 can therefore be a display or an interface for exchanging data with a computer. In the case shown here, the output unit 10 is (also) designed to send data to the control interface 13 and thereby to allow e.g. further pre-positioning of the recording unit 3.

Figure 2:
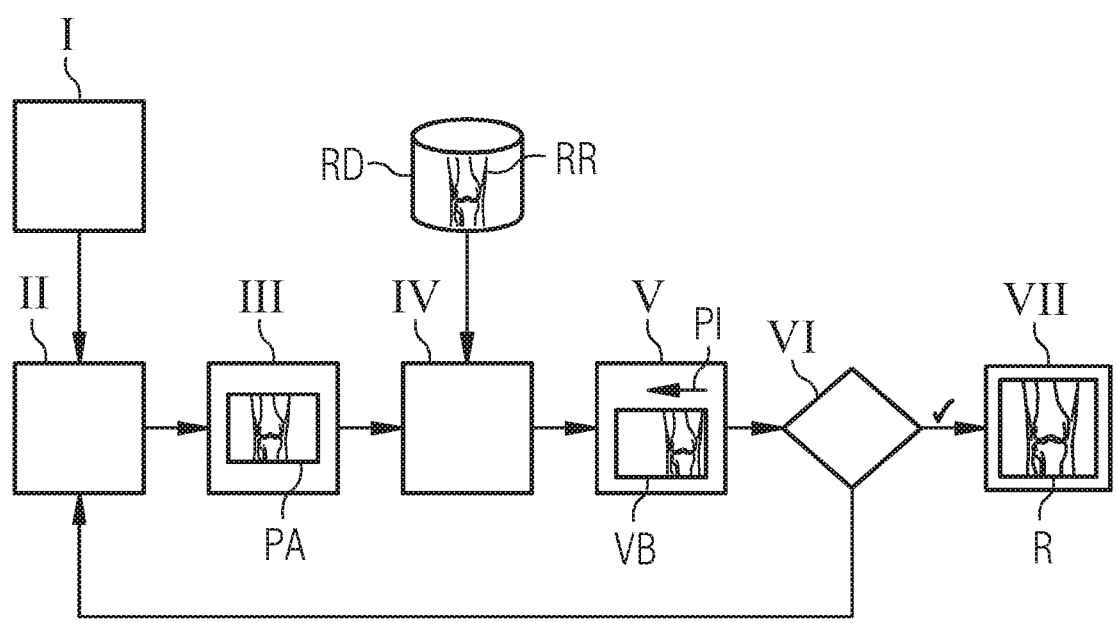
FIG. 2 shows a schematic block diagram of a preferred method sequence.

FIG. 2 shows a schematic block diagram of a preferred method sequence for positioning a body region K of a patient P for a radiography recording R via a radiography system 1 as illustrated in FIG. 1, for example.

In step I, an examination request U is provided in respect of the body region K. Here the system is told e.g. which organ is concerned and which recording is to be performed. In the following, the example case is assumed in which the examination request U is concerned with a radiography recording R of the knee.

In step II, pre-positioning takes place in respect of both the body region K in the radiography system 1 and the recording unit 3 of the radiography system 1 for the radiography recording R. The patient in the example case is requested to place their knee at a specified position, the recording unit 3 is pre-positioned above the knee in such a way that the joint space of the knee is most likely to be correctly depicted in a radiography recording R. Even if the pre-positioning appears to be correct externally, this is not necessarily the case and a "dose-free" check is then performed in accordance with an embodiment of the invention.

In step III, a positioning recording PA of the body region K is produced by making a fluoroscopy recording using the recording unit 3 and the image detector 4 while the body region is situated in the position it assumed in step II. A fluoroscopy recording of the knee is therefore obtained in the example case.

In step IV, a preview image VB is produced from the positioning recording PA and positioning information PI is produced from this preview image VB. It would also be possible to produce the positioning information PI directly from the positioning recording PA.

For the purpose of producing the positioning information PI, reference radiography images RR in a reference database RD are accessed and a correlation of the positioning recording PA or the preview image VB with these reference radiography images takes place.

In the example case, as part of processing the positioning recording PA or the preview image VB, automatic image recognition establishes that, in comparison with corresponding reference radiography images RR, the knee would be situated too far to the right. Therefore an arrow is produced as positioning information PI, indicating that the knee should be moved to the left.

In step V, the preview image VB and the positioning information PI are output.

In the present embodiment variant of the method, correction of the positioning can be achieved automatically.

In step VI, provision is made for examining whether a correct positioning is present. This is not so in the example case. Therefore part of the method is repeated starting from step II. In the example case, the knee is not moved to the left and instead the recording unit is moved to the right and the steps III to VI are repeated.

If recording unit 3 and body region K are correctly positioned relative to each other, a radiography recording R is produced in step VII.

Figure 3:
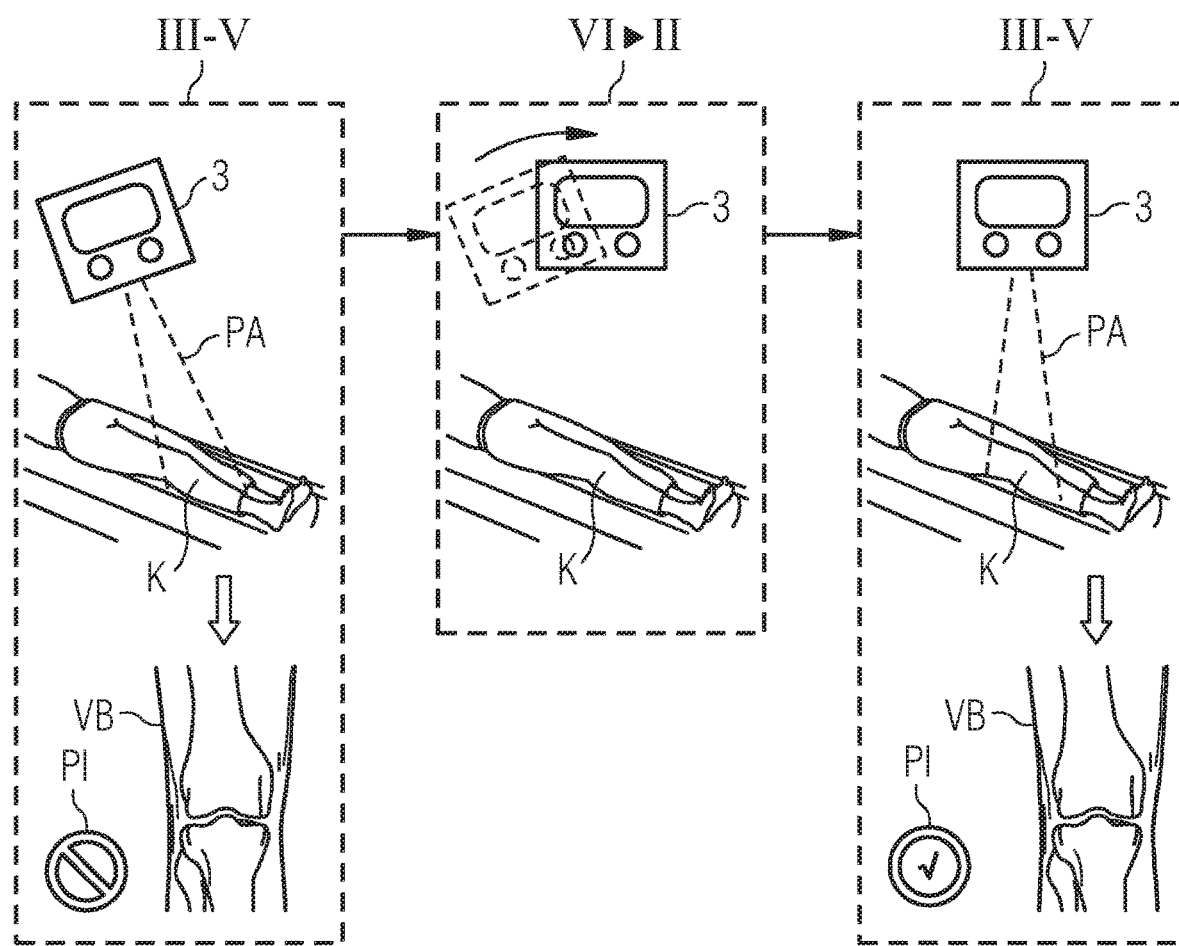
FIG. 3 shows a schematic diagram of a method sequence in practice.

FIG. 3 shows a schematic implementation of a method sequence shown in FIG. 2 in practice. In the left-hand partial diagram, the recording unit 3 and the body region K (the knee) are pre-positioned as per step II. It is already noticeable here that the recording unit 3 is to some extent tilted, though this was not registered in practice.

By way of the pre-positioned recording unit 3, a positioning recording PA of the pre-positioned knee is produced in the form of a fluoroscopy recording, whose beam cone is illustrated by broken lines. A preview image VB is generated from the positioning recording PA and then displayed. The left-hand partial diagram therefore essentially shows the method steps III to V of the method illustrated in FIG. 2.

An image processing program automatically recognized in the preview image VB that the joint space of the knee cannot be recognized, and that a radiography recording using this recording angle would therefore be unusable. This is made clear by a display of positioning information PI. In the black/white figure illustrated, this positioning information PI is designed in the form of a prohibitive sign. In practice, e.g. a red light can be used for this purpose.

In the central partial diagram, it is (possibly automatically) established that the positioning recording PA did not depict the knee correctly, or that the positioning information PI was negative and a (possibly automatic) change is applied to the presetting of the recording unit 3. The central partial diagram therefore essentially shows the method steps VI and again II of the method illustrated in FIG. 2.

In the right-hand partial diagram, the newly pre-positioned recording unit 3 again produces a positioning recording PA of the pre-positioned knee in the form of a fluoroscopy recording, whose beam cone is again illustrated by broken lines. A preview image VB is again generated from the positioning recording PA and then displayed. The right-hand partial diagram therefore again shows the method steps III to V of the method illustrated in FIG. 2.

In the preview image VB, the image processing program this time automatically recognizes that the joint space of the knee is now readily recognizable, and that a radiography recording using this recording angle would therefore be useful. This is made clear from a display of positioning information PI, a positive check symbol in this case. In practice, e.g. a green light can be used for this.

In conclusion, it is again noted that both the methods and the illustrated apparatuses or entities described in detail above are merely example embodiments, which can be modified in all manner of ways by a person skilled in the art without thereby departing from the scope of the invention. Moreover, the use of the indefinite article "a" or "an" does not preclude multiple occurrences of the feature concerned. Likewise, the terms "unit" and "module" do not preclude the relevant components consisting of a plurality of interacting subcomponents, which may also be spatially distributed if applicable.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE SIGNS

1 Radiography system
2 Motional mechanism
3 Recording unit
4 Image detector
5 Detection unit
6 Image interface
7 Pre-positioning interface
8 Recording control interface
9 Production unit
10 Output unit
11 Interface
12 Control entity
13 Control interface
14 Apparatus
K Body region
P Patient
PA Positioning recording
PI Positioning information
R Radiography recording
RR Reference radiography image RD Reference database
U Examination request
VB Preview image
I-VII Method steps

What is claimed is:

1. A method for positioning a body region of a patient for a radiography recording via a radiography system designed for recordings in a context of both radiography and fluoroscopy, the method comprising:
providing an examination request of the body region;
pre-positioning the body region in the radiography system for the radiography recording;
pre-positioning at least one of a recording unit of the radiography system and an image detector of the radiography system for the radiography recording;
producing a positioning recording of the body region via the radiography system, the radiography system being switched into a fluoroscopy mode and the positioning recording being a fluoroscopy recording;
producing positioning information from the positioning recording, the positioning information including information about a location of the body region and quality-critical criteria, the producing the positioning information including correlating the location of the body region with existing reference radiography images; and
outputting the positioning information.

2. The method of claim 1, wherein
producing a preview image from the positioning recording, the preview image depicts a preview of an image as if generated by the radiography system, and
the positioning information is produced from the preview image.

3. The method of claim 2, wherein the preview image is output together with the positioning information.

4. The method of claim 2, wherein presettings are effected in accordance with the examination request.

5. The method of claim 4, wherein the examination request includes an organ program or an organ program is provided in addition to the examination request.

6. The method of claim 2, wherein
a form of an indicator design in an event of incorrect positioning is different from an indicator design in an event of correct positioning, and
at least one of a color and a brightness of the indicator changes as soon as a correct positioning is achieved.

7. The method of claim 1, wherein
presettings of the radiography system are altered in accordance with the examination request, and
the examination request includes an organ program or an organ program is provided in addition to the examination request.

8. The method of claim 1, wherein additional recording parameters for the radiography system are specified by the examination request.

9. The method of claim 8, wherein a preview image also depicts a preview of an image generated by the recording unit using the recording parameters.

10. The method of claim 1, wherein the producing of the positioning information includes correlating a preview image with existing reference radiography images.

11. The method of claim 10, wherein an automatic examination of at least one of the positioning recording and the preview image takes place as a function of the examination request, and wherein the positioning information indicates whether the body region and the recording unit are correctly positioned for the radiography recording based on the examination request.

12. The method of claim 1, wherein the positioning recording is made via the recording unit and an image detector of the radiography system.

13. The method of claim 12, wherein the radiography system comprises a detection unit for the radiography recording.

14. The method of claim 1, wherein the outputting outputs the positioning information at least one of visually and acoustically.

15. The method of claim 14, wherein
a form of an indicator design in an event of incorrect positioning is different from an indicator design in an event of correct positioning, and
at least one of a color and a brightness of the indicator changes as soon as a correct positioning is achieved.

16. The method of claim 1, wherein the positioning information includes information indicating which settings are to be adjusted, and wherein the positioning information relating to a changed pre-positioning includes information showing whether the changed pre-positioning resulted in an improvement of the positioning.

17. The method of claim 1, the method further comprising:
performing the method of claim 1 at least one time, at least one of the body region and the recording unit being in a different position each performance of the method of claim 1.

18. The method of claim 17, wherein a different pre-positioning of the body region occurs until the positioning information displays a correct positioning of the recording unit, and a radiography recording is then made automatically, via the recording unit.

19. A non-transitory computer program product comprising a computer program, directly loadable into a storage entity of a control entity or a computing apparatus, including program sections for executing the method of claim 1 when the computer program is executed in the control entity or the computing apparatus.

20. A non-transitory computer-readable medium, storing program sections, readable in and executable by a computer unit to execute the method of claim 1 when the program sections are executed by the computer unit.

21. An apparatus for positioning a body region of a patient for a recording via a radiography system designed for recordings in both radiography and fluoroscopy, the apparatus comprising:
a data interface configured to receive an examination request in respect of the body region;
an interface configured to control a motional unit for pre-positioning a recording unit of the radiography system;
an interface configured to control production of a positioning recording of the body region via the radiography system;
an interface configured to receive fluoroscopy recordings from the radiography system;
a production unit configured to produce positioning information from the positioning recording, the positioning information including information about a location of the body region and quality-critical criteria, the producing the positioning information including correlating the location of the body region with existing reference radiography images; and
an output unit configured to output the positioning information.

22. The apparatus of claim 21, further comprising:
a reference database including reference radiography images, wherein the production unit is configured to correlate a preview image based on this positioning recording with the reference radiography images of the reference database.

23. The apparatus of claim 22, wherein the production unit is also configured to perform an automatic examination of at least one of the positioning recording and the preview image as a function of the examination request and to produce positioning information indicating whether the body region and the recording unit are correctly positioned for the radiography recording based on the examination request.

24. A control entity for a radiography system, comprising the positioning apparatus of claim 21.

25. A radiography system comprising the control entity of claim 24.

* * * * *